United States Patent [19]

Carr

[11] 4,205,080

[45] May 27, 1980

[54] 2,3-DIHYDRO BENZOFURAN CARBOXAMIDES

[75] Inventor: John B. Carr, Houston, Tex.

[73] Assignee: Shell Oil Company, Houston, Tex.

[21] Appl. No.: 39,624

[22] Filed: May 16, 1979

Related U.S. Application Data

[63] Continuation-in-part of Ser. No. 938,610, Aug. 31, 1978, abandoned, which is a continuation-in-part of Ser. No. 817,898, Jul. 31, 1977, abandoned.

[51] Int. Cl.$^2$ .................... A61K 31/38; A61K 31/34; C07D 307/85

[52] U.S. Cl. .................... 424/275; 424/285; 260/346.73; 549/60

[58] Field of Search .................... 260/346.73, 332.2 A; 424/285, 275

[56] References Cited

U.S. PATENT DOCUMENTS 4,087,542  5/1978  Cragoe, Jr. et al. .................... 424/275

Primary Examiner—Henry R. Jiles
Assistant Examiner—Bernard Dentz

[57] ABSTRACT

Certain 5-(or 4-)substituted 2,3-dihydro-N-(2-propenyl)-2-benzofurancarboxamides, useful as lipogenesis inhibitors in mammals.

2 Claims, No Drawings

2,3-DIHYDRO BENZOFURAN CARBOXAMIDES

This application is a continuation-in-part of application Ser. No. 938,610, filed Aug. 31, 1978, which was a continuation-in-part of application Ser. No. 817,898, filed on Jul. 21, 1977, both now abandomed.

DESCRIPTION OF THE INVENTION

It has been found that lipogenesis in mammals is inhibited by 5-(or 4-)substituted 2,3-dihydro-N-(2-propenyl)-benzofurancarboxamides described by the formula:

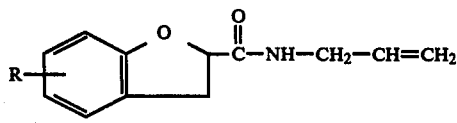

wherein
- (a) R is bonded to the carbon atom at the 5-position in the molecule, and is cycloalkyl of from three to six carbon atoms; alkyl of from four to eight carbon atoms; thienyl; or phenyl, phenoxy, benzyl or benzoyl or any of these substituted by one of alkyl or alkoxy of from one to six carbon atoms, acetamido, 1-hydroxyethyl, and nitro.
- (b) R is bonded to the carbon atom at the 4-position in the molecule, and is phenoxy or substituted phenoxy as indicated above.

In these compounds, each alkyl moiety may be of straight-chain or branched-chain configuration.

For illustration, preparation of typical individual species of genus defined by Formula I are described in the examples included hereinafter. Other typical, illustrative individual species of this genus and those wherein the moiety R is one of the following, the number in each case indicating the position of the carbon atom in the ring to which the moiety R is bonded:
- (a) 5-(4-methoxyphenyl)
- (b) 5-(p-tolyl)
- (c) 5-benzoyl
- (d) 5-(2-thienyl)
- (e) 5-(1,1,3,3-tetramethylbutyl)
- (f) 5-(4-nitrophenyl)

Chirality exists in these compounds, hence they can exist in two optical isomeric forms. None of the isomers has been separated, nor has the lipogenesis inhibiting activity of any of the individual isomers been determined. The individual species that have been prepared inhibit lipogenesis. Under the circumstances, the invention contemplates the active individual isomers, as well as mixtures thereof.

Compounds of formula I can be prepared by treating an alkyl, suitably ethyl, ester of the corresponding carboxylic acid, in solution in a suitable solvent such as ethanol, with 2-propenamine. The reaction will go forward at room temperature; however, higher temperatures—for example, the mixture can be refluxed—may be employed to reduce the reaction time. Preferably, about a four-to-six fold excess of the amine is used. The desired product can be recovered by evaporating the solvent and excess amine, then employing conventional techniques such as selective extraction, recrystallization and/or dry column chromatography, to isolate the desired product.

Certain of the ethyl ester precursors are known: Witiak, D. T., et al., Lipids, 11(5), 384–391 (1976); methods for preparing such esters are described therein and in references cited therein.

In general, the precursor esters can be prepared as follows:
- (a) the ethyl ester of the appropriate benzofurancarboxylic acid is prepared by condensation of the appropriate R-substituted salicylaldehyde with diethyl bromomalonate in the presence of potassium carbonate, according to the method of Kurkudar and Rao, Indian Acad. Sci., Section A, 58, 336 (1963).
- (b) hydrolysis of the ester to the corresponding acid, also as shown in Kurkudar and Rao and in Witiak, supra.
- (c) reduction of the acid to the 2,3-dihydrobenzofurancarboxylic acid, by use of sodium/mercury amalgam, according to the method of Fredga, Acta Chem. Scand., 9, 719 (1955).
- (d) Fisher-Speier esterification of the acid with ethanol, i.e., treating the acid with ethanol in a solvent such as toluene, in the presence of a catalytic amount of an acid such as sulfuric acid, hydrochloric acid, or para-toluene-sulfonic acid.

The precursor R-substituted salicylaldehydes can be prepared by treating the appropriate phenol with chloroform under strongly basic conditions, according to Reimer-Tiemann Reaction. (References cited in The Merck Index, 9th edition, page ONR-74; also, Russell, A. and Lockhart. L. B., Organic Synthesis, 22, 63 (1942)).

Many of the precursor phenols are known compounds; others can be prepared by conventional procedures. Thus, the precursor phenols for the species of Examples 2, 3, 4, 5, and species (c) and (e) are commercially available; the phenols for species (b) and (g) are disclosed in Beilstein. Alpha-(4-hydroxyphenyl)thiophene, the precursor phenol for species (d), can be prepared by either or both of the methods disclosed by M. A. Al'perovich, et al, Zh. Obschch. Khim., 34, 645–50 (1964); Chem. Abst., 60, 14639d (1964)), and Y. Admad, et al., Canadian Journal of Chemistry, 45, 1539–42 (1967).

The salicylaldehyde for the species of Example 5 is prepared by the Reimer-Tiemann treatment of 3-phenoxyphenol.

Species (a) can be prepared by: (1) Baeyer-Villiger oxidation of the 4-acetylphenyl species to form the 4-(acetyloxy)derivative; (2) hydrolysis of the acetyloxy derivatives to form the 4-hydroxy derivative; (3) etherification of the hydroxy derivative.

Preparation of compounds of Formula I is illustrated in the following examples. In each case, the identities of the product, and of the precursor(s) involved, were confirmed by appropriate chemical and spectral analyses.

EXAMPLE 1

Preparation of 2,3-dihydro-5-phenyl-N-(2-propenyl)-2-benzofurancarboxamide (1)

22 g of p-phenylphenol was dissolved in 95% ethanol; a solution of 40 g of sodium hydroxide in 80 ml of water was rapidly added. The resulting solution was heated to 75°–80° C. and 20 ml of chloroform was added over a one-hour period, the mixture being gently refluxed. The mixture then was stirred for three hours, cooled and the ethanol and excess chloroform were evaporated under reduced pressure. The resulting residue was cooled and poured into cold water. The resulting mixture was acidified by slow addition of hydrochloric acid and extracted with ether. The solvent was evaporated from the extract under reduced pressure, the residue was poured in twice its volume of saturated sodium metabisulfite solution and the mixture was shaken vigorously for forty-five minutes. The resulting semisolid bisulfite addition compound was allowed to stand for one hour, filtered in the dark and washed with small portions of ethanol and ether to remove the phenol. The bisulfite addition compound with decomposed with dilute sulfuric acid, the mixture being warmed on a water-bath for thirty minutes. The cooled mixture was extracted with ether, dried ($Na_2SO_4$), and the solvent was evaporated under reduced pressure. The residue was treated with activated charcoal and recrystallized from ethanol/water to give 5-phenylsalicylaldehyde (1A). as yellow crystals, mp: 98°–99° C.

A mixture of 0.99 g of 1A, 0.96 g of diethyl bromomalonate and 1.25 g of anhydrous potassium carbonate in 20 ml of 2-butanone, was refluxed for 10 hours. The solvent was evaporated under reduced pressure. The residue was cooled, poured into 100 ml of water and extracted with ether. The extract was washed with cold 5% sodium hydroxide solution and water and then concentrated under reduced pressure. The residue was recrystallized from ethanol to give ethyl 5-phenylbenzofuran-2-carboxylate (1B), as white crystals, mp: 109°–110° C.

A mixture of 1.3 g of Compound 1B and 50 ml of 10% alcoholic potassium hydroxide was refluxed for 4 hours. The solvent was evaporated under reduced pressure and the residue was washed with ether and dissolved in water. The basic solution was acidified with dilute hydrochloric acid and extracted with ether. The ether layer was extracted with dilute sodium bicarbonate solution. The aqueous solution was re-acidified with dilute hydrochloric acid and extracted with ether. The ether extract was dried ($Na_2SO_4$) and concentrated under reduced pressure. The residue was crystallized from ethanol to give 5-phenyl-2-benzofurancarboxylic acid (1C), as white solid, mp: 220°–221° C.

5.0 g of 1C was mixed with 90 ml of 10% sodium hydroxide solution. Sodium amalgam (prepared from 1.5 g of sodium and 50 g of mercury) was added to the stirred mixture over a period of one hour. The mixture was then stirred for 24 hours and allowed to stand at room temperature for an additional 24 hours. The mercury was separated, the solution was neutralized with dilute hydrochloric acid and extracted with ether. The extract was dried ($Na_2SO_4$) and concentrated under reduced pressure. The residue was recrystallized from ethanol to give 2,3-dihydro-5-phenyl-2-benzofurancarboxylic acid (1D), as white crystals, mp: 186°–187° C.

A mixture of 2.5 g of 1D, 60 ml of ethanol, 20 ml of dry benzene and 2 ml of concentrated sulfuric acid was refluxed for seven hours, with removal of water as it formed. The resulting mixture was concentrated, and the residue dissolved in ether. The solution was washed with saturated sodium bicarbonate solution and water. The aqueous portion was extracted with ether. The combined organic layers were dried ($Na_2SO_4$) and the solvent was evaporated under reduced pressure. The residue was distilled to give ethyl 2,3-dihydro-5-phenylbenzofuran-2-carboxylate (1E), as a colorless liquid, bp: 180°–181° C., 0.35 Torr.

An ethanol solution of 1E and an excess of 2-propenamine was refluxed for 2.5 days. The excess amine and the solvent were evaporated under reduced pressure. The resulting gum was recrystallized from methylene chloride/hexane to give 1, as a white solid, mp: 112° C.

EXAMPLES 2–6

By procedures similar to those described in Example 1, the following additional individual species of the class of compounds defined in Formula I were prepared:

| Example No. | Compound No. | R (number indicating position on ring) | Melting Point (°C.) |
|---|---|---|---|
| 2 | 2 | 5-(1-methylpropyl) | not determined |
| 3 | 3 | 5-cyclohexyl | 92–93 |
| 4 | 4 | 5-benzyl | 92–93 |
| 5 | 5 | 4-phenoxy | 55–57 |

In the case of Compound 5, the precursor salicylaldehyde was prepared as follows:

145.0 g of meta-phenoxyphenol was dissolved in 700 ml of 95% ethanol. 468 g of sodium hydroxide was then added rapidly. The resulting suspension was heated to 70°–80° C. Then 558.7 g of chloroform was added, at such a rate that gentle reflux was maintained (the addition required 10 hours). The mixture then was stirred for 2 hours at 75°–80° C., held at room temperature overnight and then was filtered. The solid product was dissolved in 1000 ml of water. The solution was acidified to pH=2 with concentrated hydrochloric acid, then was extracted with ether. The ether layer was dried ($MgSO_4$) and concentrated. The residue was extracted with hot petroleum ether. The extract was dried ($Na_2SO_4$) and concentrated to give an oil, which was wet column chromatographed over silica gel, using a 9/1 v/v mixture of petroleum ether and ether as eluent, then using a 4/1/ v/v mixture of petroleum ether and ether as eluent. The fourth fraction obtained was identified as 2-hydroxy-6-phenoxybenzaldehyde.

EXAMPLE 6

2,3-Dihydro-5-(4-(1-hydroxyethyl)phenyl)-N-(2-propenyl)-2-benzofurancarboxamide (6)

12.2 g of acetyl chloride was added to a mixture of 10.3 g of 1B, and 120 ml of carbon disulfide, then 21.8 g of anhydrous aluminum chloride was added in portions to the stirred mixture. The mixture then was stirred at room temperature for 2.5 hours, the temperature rising to 32° C. The mixture was poured into 1 liter of ice water, the mixture was stirred for 30 minutes, and the solution was extracted with ether. The extract was dried ($MgSO_4$) and concentrated. The residue was washed with ether and dried. It was dissolved in 100 ml of chloroform, the solution was treated with a decolorizing agent, and 100 ml of hexane was added. The resulting solution was concentrated to about 100 ml and cooled to give ethyl 5-(4-acetylphenyl)benzofuran-2-carboxylate (6A), mp: 105°–107° C.

1.2 g of sodium borohydride was added in one portion to a stirred mixture of 15.0 g of 6A, 200 ml of ether and 40 ml of ethanol. The mixture was stirred at room temperature for 2 hours. The solvents were evaporated under reduced pressure. 1.6 liters of water was added to the residue and the mixture was extracted with chloroform. The extract was dried ($MgSO_4$), filtered and the solvent was evaporated under reduced pressure. The residue was dissolved in 150 ml of chloroform. The solution was filtered through charcoal. 400 ml of hexane was added. The solid which formed was collected, recrystallized from a 3/50 v/v mixture of chloroform and hexane and dried in a vacuum oven to give ethyl 5-(4-(1-hydroxyethyl)phenyl)-2-benzofurancarboxylate (6B), mp: 108°–109° C.

75 ml of ethanol was added to a solution of 23.9 g of 6B in 300 ml of tetrahydrofuran, then 195.7 g of 2.5% sodium/mercury amalgam was added in portions, at room temperature. The mixture was stirred at room temperature overnight. The mercury was separated, the solid was collected and dissolved in 300 ml of water. The solution was acidified to pH=1 with concentrated hydrochloric acid. The solid was collected, washed with water and dried ($P_2O_5$; reduced pressure, 45° C.). The product was dissolved in tetrahydrofuran, the solution was filtered and its volume reduced to 30 ml by evaporating the solvent under reduced pressure. The resulting solution was triturated with ether. The solid was collected and dried in a vacuum oven over $P_2O_5$ to give 2,3-dihydro-5-(4-(1-hydroxyethyl)phenyl)-2-benzofurancarboxylic acid (6C), mp: 155°–157° C.

23.3 g of methyl iodide and 7.6 g of potassium carbonate were added to a mixture of 7.8 g of 6C, 200 ml of acetone and 50 ml of dimethylsulfoxide. The resulting suspension was heated under reflux for 2 hours. The mixture was filtered and the filtrate was concentrated under reduced pressure. The residue was stirred with 400 ml of water, the water was decanted, and the residue was dissolved in tetrahydrofuran. The solution was filtered and the filtrate was concentrated. The residue was mixed with 50 g of silica gel and purified by dry column chromatography, a 9/1 v/v chloroform/tetrahydrofuran mixture being used as eluent. The band containing product was extracted with tetrahydrofuran, the solvent was evaporated from the extract under reduced pressure and the residue was dried in a vacuum oven. The residue was stirred with ether and the solid was collected and dried to give methyl 2,3-dihydro-5-(4-(1-hydroxyethyl)phenyl)-2-benzofurancarboxylate (6D), mp: 98°–100° C.

15 ml of 2-propenylamine was added to a mixture of 5.0 g of 6D and 100 ml of methanol. The solution was stirred at room temperature overnight. The volatile materials were evaporated under reduced pressure. The residue was stirred with 50 ml of ether, the solid was collected and dried in a vacuum oven to give 6, mp: 122°–124° C.

EXAMPLE 7

5-(4-(Acetylamino)phenyl)-2,3-dihydro-N-(2-propenyl)-2-benzofurancarboxamide (7)

A mixture of 6.2 g of 6A, 100 ml of ethanol and 200 ml of tetrahydrofuran was heated to 60°–70° C. A solution of 1.53 g of hydroxylamine hydrochloride and 1.16 g of sodium carbonate in 20 ml of water and added. The mixture was heated for 3 hours at 60°–70° C. 1.53 g of hydroxyamine hydrochloride and 1.16 g of sodium carbonate in 20 ml of water was added and the mixture was heated at 60°–70° C. for 4 hours. 1.53 g of hydroxylamine and 1.16 g of sodium carbonate in 20 ml of water was added and the mixture heated at 60°–70° C. for 4 hours. The solid was collected, washed with water, then ethanol, and extracted with methylene chloride. The solvent was evaporated from the extract under reduced pressure to give ethyl 5-(4-(1-hydroxyimino)ethyl)phenyl-2-benzofurancarboxylate (7A), mp: 220°–222° C.

56.5 g of phosphorus pentachloride was added in portions to a solution of 55.0 g of 7A in 1 liter of chloroform, and the mixture was stirred at room temperature for 16 hours. The solvent was evaporated under reduced pressure. The residue was suspended in 4 liters of water, the mixture was stirred vigorously for 30 minutes and filtered. The solid was extracted with chloroform. The extract was washed, successively, with water, saturated sodium bicarbonate solution, and water, then was filtered through celite (to break down the emulsion). The filtrate was dried ($MgSO_4$) and the solvent was evaporated under reduced pressure. The residue was triturated with ether and separated. The filtrate was concentrated to about half its volume under reduced pressure and allowed to stand over a weekend. The solid which formed was collected and dissolved in 400 ml of chloroform. The solution was filtered over charcoal, and diluted with 400 ml of hexane. The solid was collected, and dry column chromatographed over silica gel, using a 1/9 v/v mixture of tetrahydrofuran and chloroform as eluent. The appropriate fractions were combined and extracted with tetrahydrofuran. The solvent was evaporated under reduced pressure and the residue was triturated with ether. The solid was collected and dried under reduced pressure to give ethyl 5-(4-acetylamino)phenyl)-2-benzofurancarboxylate (7B), mp: 174°–176° C.

25 ml of ethanol was added to a mixture of 2.3 g of 7B in 80 ml of tetrahydrofuran. Then 18.8 g of 2.5% sodium amalgam was added in portions, and the mixture was stirred for 20 hours. The mercury was separated and the solvent was evaporated under reduced pressure. The residue was dissolved in 350 ml of water, the solution was filtered, and concentrated hydrochloric acid was added until the solution had a pH of 2. The solid was collected, washed with water and dried under reduced pressure. The residue was stirred with 30 ml of acetone. The solid was collected and refluxed with acetone. The solution was filtered and the filtrate was concentrated to a small volume under reduced pressure. The solid was collected and dried, to give 5-(4-(acetylamino)phenyl)-2,3-dihydro-2-benzofurancarboxylic acid (7C), mp: 274°–276° C.

5 drops of concentrated sulfuric acid was added to a mixture of 3.2 g of 7C and 150 ml of ethanol. The mixture was heated under reflux, using a Soxhlet extractor filled with molecular sieve (3A). After 4 hours, the solvent was evaporated under reduced pressure, and the residue was dissolved in chloroform. The solution was washed with saturated sodium bicarbonate solution, dried ($MgSO_4$) and the solvent was evaporated under reduced pressure. The residue was dry column chromatographed over silica gel, using chloroform as eluent. The product was extracted with tetrahydrofuran and the solvent was evaporated under reduced pressure. The residue was stirred in ether. The solid was collected and refluxed in ether. The solid was collected and dried under reduced pressure to give ethyl 5-(4-(acetylamino)phenyl)-2,3-dihydro-2-benzofurancarboxylate (7D), mp: 164°–166° C.

20 ml of ethanol was added to a mixture of 1.6 g of 7D and 20 ml of 2-propenylamine. The mixture was stirred for 3 hours at room temperature. The solid which formed was collected, washed with ethanol, then ether and dried under reduced pressure to give 7, mp: 244°–247° C.

Compounds 1–7 have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical for a period of time, then isolating the lipid from the treated tissue and determining the up-take of the radioactive carbon by means of scintillation counting techniques. These tests were conducted in swine adipose tissue because in swine, the primary site of lipogenesis—i.e., fatty acid synthesis—appears to be adipose tissue.

Described in more detail, the tests were conducted according to the following general procedure:

150 milligrams of slices of swine adipose tissue were incubated at 37° C. for 2 hours with shaking in 3 milliliters of Krebs-Ringer bicarbonate solution containing one-half of the normal calcium ion concentration, 60 micromoles of glucose, 0.5 micro-Curie of glucose-U$^{14}$C, and 300 microunits of insulin, and 5% dimethyl sulfoxide (DMSO). The test compound was added as a solution or suspension in DMSO and was present as a concentration of 100 micrograms per milliliter of incubation mixture.

The incubation was terminated by addition of 0.25 milliliter of 1 N sulfuric acid. The resulting mixture was extracted with a total of 25 milliliters of chloroform:methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compound. The data obtained are reported as the percent inhibition of lipogenesis compared to the results obtained in the control tests wherein only the test compound was omitted. The results are summarized in Table I.

Table I

| Compound | Percent Inhibition |
|---|---|
| 1 | 59 |
| 2 | 66 |
| 3 | 43 |
| 4 | 64 |
| 5 | 77 |
| 6 | 40 |
| 7 | 76 |

Compounds of Formula I can be used to inhibit lipogenesis in mammals such as, for example, pets, animals in zoo, livestock, furbearing animals and domestic animals, including, but not limited to dogs, cats, mink, sheep, swine, cattle, horses, mules and donkeys. The effect is obtained by administering an effective amount of one or a mixture of the inhibitors orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the inhibitor needed to inhibit lipogenesis will depend upon the particular compound(s) used, and the particular animal being treated. However, in general, satisfactory results are obtained when the inhibitor is administered in a dosage of from about 1 to about 500 milligrams per kilogram of the animal's body weight. The inhibitor can be administered in a single dose or in a series of doses in the same day, or over a period of days. For any particular animal, a specified dosage regimen should be adjusted according to the individual need, the particular inhibitor used, and the professional judgement of the person administering or supervising the administration of the inhibitor. It is to be understood that the dosages set forth herein are exemplary only, and that they do not, to any extent, limit the scope or practice or the invention.

The invention claimed:

1. A compound of the formula:

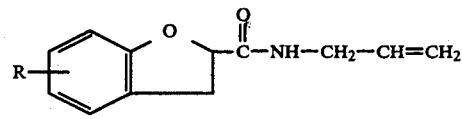

wherein
(a) R is bonded to the carbon atom at the 5-position in the molecule, and is cycloalkyl of from three to six carbon atoms; alkyl of from four to eight carbon atoms; thienyl; or phenyl, phenoxy, benzyl or benzoyl or any of these substituted by one of alkyl or alkoxy of from one to six carbon atoms, acetamido, 1-hydroxyethyl, and nitro;
(b) R is bonded to the carbon atom at the 4-position in the molecule, and is phenoxy or substituted phenoxy as indicated above.

2. A method of inhibiting lipogenesis in a mammal, which comprises administering orally or parenterally an effective amount of a compound of claim 1.

* * * * *